(12) United States Patent
Milton et al.

(10) Patent No.: US 6,552,021 B2
(45) Date of Patent: Apr. 22, 2003

(54) PHARMACEUTICAL COMPOUNDS

(75) Inventors: John Milton, Slough (GB); Nigel Vicker, Slough (GB); William Alexander Denny, Auckland (NZ); Swarnalatha Akuratiya Gamage, Auckland (NZ); Julie Ann Spicer, Auckland (NZ)

(73) Assignee: Xenova Limited (GB)

( * ) Notice: Subject to any disclaimer, the term of this patent is extended or adjusted under 35 U.S.C. 154(b) by 0 days.

(21) Appl. No.: 09/797,902

(22) Filed: Mar. 5, 2001

(65) Prior Publication Data

US 2001/0034346 A1 Oct. 25, 2001

(30) Foreign Application Priority Data

Mar. 6, 2000 (GB) .............................................. 0005366

(51) Int. Cl.$^7$ ..................... C07D 471/04; C07D 487/04; A61K 31/4985; A61D 35/00
(52) U.S. Cl. ..................... 514/250; 544/233; 544/251; 544/343
(58) Field of Search .................. 514/250; 544/233, 544/251, 343

(56) References Cited

U.S. PATENT DOCUMENTS

| | | | |
|---|---|---|---|
| 6,262,075 B1 * | 7/2001 | MacKenzie et al. | 514/316 |
| 6,268,163 B1 * | 7/2001 | Kongsbak et al. | 435/15 |
| 6,312,622 B1 * | 11/2001 | Erion et al. | 424/9.1 |
| 6,337,344 B1 * | 1/2002 | Defossa et al. | 514/415 |
| 6,344,505 B1 * | 2/2002 | Valentine et al. | 524/91 |
| 6,369,235 B1 * | 4/2002 | Michejda et al. | 548/310.4 |

OTHER PUBLICATIONS

Rewcastle, G.W. et al, J. Med. Chem., 30, 1987, 843–851.*
Draetta, G. and Pagano, M. in "Annual Reports in Medicinal Chemistry, vol. 31", 1996, Academic Press, San Diego, p241–246.*

* cited by examiner

*Primary Examiner*—Richard L. Raymond
*Assistant Examiner*—Thomas McKenzie
(74) *Attorney, Agent, or Firm*—Nixon Vanderhye P.C.

(57) ABSTRACT

A compound which is a heteroaromatic[a]phenazine carboxamide derivative of formula (I)

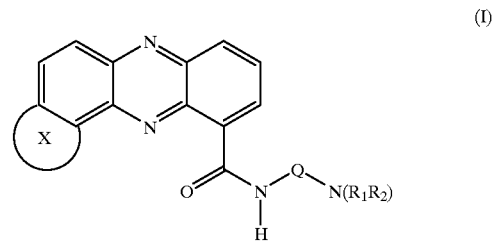

(I)

wherein X is a five- or six-membered heteroaromatic ring which contains one or two nitrogen atoms and which is unsubstituted or substituted by $C_1$–$C_6$ alkyl, hydroxyl or $C_1$–$C_6$ alkoxy;

Q is $C_1$–$C_6$ alkylene which is unsubstituted or substituted by $C_1$–$C_6$ alkyl which is unsubstituted or substituted by a hydroxy group; and $R_1$ and $R_2$ which are the same or different are each $C_1$–$C_6$ alkyl;

or a pharmaceutically acceptable salt thereof. These compounds are inhibitors of topoisomerase I and II and can be used to treat tumours, including tumours which express MDR.

14 Claims, No Drawings

PHARMACEUTICAL COMPOUNDS

The present invention relates to heteroaromatic[a] phenazine carboxamides and derivatives thereof. These compounds are cytotoxic agents which have demonstrated topoisomerase I and topoisomerase II inhibition and have the ability to circumvent multidrug resistance mechanisms. They are therefore potential anticancer agents.

The topoisomerases are important cellular targets for a number of successful chemotherapeutic agents (Wang, Ann. Rev. Biochem, 65, 635–692, 1996) and are essential enzymes in the regulation of DNA topology which is required if cells are to divide and proliferate (Wang, loc cit). Drugs that target topoisomerase II, for example doxorubicin and etoposide, have been widely used in cancer chemotherapy (Hande, Biophys. Acta 1400, 173–184, 1998) while those that specifically target topoisomerase I, principally the camptothecin analogues, have made an important impact more recently, an example being CPT-11 for the treatment of colon cancer (Dancey et al, Br. J. Cancer 74, 327–338, 1996). More recently, topoisomerases have been shown to be therapeutic targets for antifungal, antibacterial and antiviral drugs (Chen et al, Rev. Pharmacol. Toxicol, 34, 191–218, 1994).

In addition to those compounds that specifically target topoisomerase I or II, several joint inhibitors of topoisomerase I and II have been identified and may also be beneficial in the treatment of solid tumours. These compounds include intoplicine (Riou et al, Cancer Res. 53, 5987–5993, 1993), DACA/XR5000 (Finlay et al, Eur. J. Cancer 32A, 708–714, 1996) and TAS-103 (Utsugi et al, J. Cancer Res, 88, 992–1002 1997) which are all in clinical evaluation. The advantage of joint inhibitors of topoisomerase I and II is their ability to avoid drug resistance and to target two key enzymes that affect the topology of DNA which are active at different points in the cell cycle.

It has now been found that a class of novel heteroaromatic[a]phenazine carboxamides are inhibitors of topoisomerase I and topoisomerase II. Accordingly, the present invention provides a compound which is a heteroaromatic[a]phenazine carboxamide derivative of formula (I)

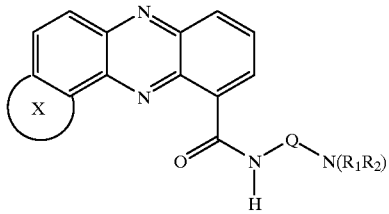

(I)

wherein X is a five- or six-membered heteroaromatic ring which contains one or two nitrogen atoms and which is unsubstituted or substituted by $C_1$–$C_6$ alkyl, hydroxyl or $C_1$–$C_6$ alkoxy;

Q is $C_1$–$C_6$ alkylene which is unsubstituted or substituted by $C_1$–$C_6$ alkyl which is unsubstituted or substituted by a hydroxy group; and $R_1$ and $R_2$, which are the same or different are each $C_1$–$C_6$ alkyl;

or a pharmaceutically acceptable salt thereof.

In a preferred aspect of the invention the heteroaromatic [a]phenazine carboxamide derivative is of formula (Ia)

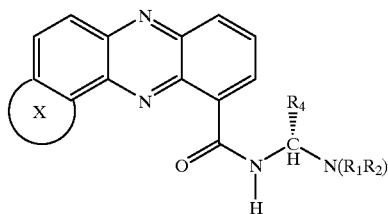

(Ia)

wherein $R_1$ and $R_2$ are as defined above and $R_4$ is $C_1$–$C_6$ alkyl which is unsubstituted or substituted by hydroxy.

When X in formula (I) and (Ia) is a six-membered heteroaromatic ring which is substituted, it is typically substituted on a ring carbon atom. Preferably it is substituted at this position by $C_1$–$C_6$ alkoxy or hydroxy. When X in formula (I) or (Ia) is a five-membered heteroaromatic ring it is typically substituted on a ring nitrogen atom by $C_1$–$C_6$ alkyl. Suitable examples of six-membered heteroaromatic rings are pyridine and pyrazine. Suitable examples of five-membered heteroaromatic rings are pyrrole and pyrazole.

A $C_1$–$C_6$ alkyl group may be linear or branched. A $C_1$–$C_6$ alkyl group is typically a $C_1$–$C_4$ alkyl group, for example a methyl, ethyl, propyl, i-propyl, n-butyl, sec-butyl or tert-butyl group. A $C_1$–$C_6$ alkyl group is unsubstituted or substituted, typically by one or more groups selected from hydroxy, hydroxy-$C_1$–$C_6$ alkyl wherein the alkyl moiety is unsubstituted or substituted as specified herein for $C_1$–$C_6$ alkyl. Examples of hydroxy-$C_1$–$C_6$-alkyl include, for instance, hydroxymethyl, 1-hydroxyethyl and 2-hydroxyethyl. $C_1$–$C_6$ alkylene is a $C_1$–$C_6$ alkyl group as defined above which is divalent.

A $C_1$–$C_6$ alkoxy group may be linear or branched. It is typically a $C_1$–$C_4$ alkoxy group, for example a methoxy, ethoxy, propoxy, i-propoxy, n-propoxy, n-butoxy, sec-butoxy or tert-butoxy group.

In formula (Ia) $R_4$ is preferably $C_1$–$C_6$ alkyl, more preferably methyl.

In formulae (I) and (Ia) a preferred option for Q is a $C_2$- or $C_3$-alkylene chain which is substituted α to the adjacent amide nitrogen atom by $C_1$–$C_6$ alkyl which is unsubstituted or substituted as defined above. Preferably the substituent on Q is unsubstituted $C_1$–$C_6$ alkyl or hydroxy-$C_1$–$C_6$ alkyl such as hydroxymethyl. Typically the $C_2$- or $C_3$-alkylene chain is substituted α to the adjacent amide nitrogen atom by methyl, ethyl, isopropyl, hydroxymethyl, substituted hydroxymethyl or 1-hydroxyethyl.

Examples of preferred compounds of the invention are as follows.

| Compound Name | Compound number |
| --- | --- |
| Pyrido[2,3-α]phenazine-11-carboxylic acid (2-dimethylamino-ethyl)-amide | 1 |
| Pyrido[4,3-α]phenazine-11-carboxylic acid (2-dimethylamino-ethyl)-amide | 2 |
| Pyrido[3,2-α]phenazine-11-carboxylic acid (2-dimethylamino-ethyl)-amide | 3 |
| Pyrazino[2,3-α]phenazine-11-carboxylic acid (2-dimethylamino-ethyl)-amide | 4 |
| 4-Methoxypyrido[4,3-α]phenazine-11-carboxylic acid (2-dimethylamino-ethyl)-amide | 5 |
| 4-Methoxypyrido[4,3-α]phenazine-11-carboxylic acid (2-dimethylamino-1-(R)-methyl-ethyl)-amide | 6 |
| Pyrido[3,4-α]phenazine-11-carboxylic acid (2- | 7 |

-continued

| Compound Name | Compound number |
|---|---|
| dimethylamino-ethyl)-amide | |
| 4-Methoxypyrido[2,3-α]phenazine-11-carboxylic acid (2-dimethylamino-ethyl)-amide | 8 |
| 4-Methoxypyrido[4,3-α]phenazine-11-carboxylic acid (2-dimethylamino-1-(S)-hydroxymethyl-ethyl)-amide | 9 |
| 4-Hydroxypyrido[4,3-α]phenazine-11-carboxylic acid (2-dimethylamino-ethyl)-amide | 10 |
| 4-Hydroxypyrido[2,3-α]phenazine-11-carboxylic acid (2-dimethylamino-ethyl)-amide | 11 |
| 3-Methyl-3H-Pyrazolo[4,3-α]phenazine-10-carboxylic acid (2-dimethylamino-ethyl)-amide | 12 |
| 1-Methyl-1H-pyrazolo[3,4-α]phenazine-10-carboxylic acid (2-dimethylamino-ethyl)-amide | 13 |
| 1H-Pyrazolo[3,4-α]phenazine-10-carboxylic acid (2-dimethylamino-ethyl)-amide | 14 |
| 3H-Pyrazolo[4,3-α]phenazine-10-carboxylic acid (2-dimethylamino-ethyl)-amide | 15 |
| 1H-Imidazo[4,5-α]phenazine-10-carboxylic acid (2-dimethylamino-ethyl)-amide | 16 |
| 3-Methyl-3H-pyrrolo[3,2-α]phenazine-10-carboxylic acid (2-dimethylamino-ethyl)-amide | 17 |

Compounds of formula (I) may be prepared by a process which comprises:
a) treating an activated derivative of a compound of formula (II)

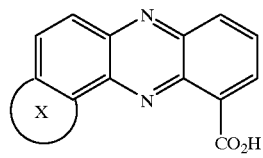

(II)

wherein X is as defined above, with a compound of formula (III)

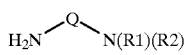

(III)

wherein Q, $R_1$ and $R_2$ are as defined above; and
(b) if desired, converting one resulting heteroaromatic (a)phenazine carboxamide derivative of formula (I) into another such derivative, and/or converting a heteroaromatic[a]phenazine carboxamide derivative of formula (I) into a pharmaceutically acceptable salt thereof.

The optical purity of resulting compounds that have an optically active centre, for instance the heteroaromatic[a]phenazine carboxamide derivatives of formula (Ia) and the salts thereof, may be determined by the addition of an NMR shift reagent such as 2,2,2-trifluoro-1 (9-anthryl) ethanol to NMR samples of the homochiral compounds.

The starting compounds of formula (II) are novel and thus constitute a further aspect of the present invention.

In step (a) the carboxylic acid grouping in formula (II) may be activated as the corresponding acid chloride which may be obtained by treating the free carboxylic acid of formula (II) with thionyl chloride. Alternatively the carboxylic acid grouping can be activated by treatment with an appropriate amide-coupling reagent such as 1,1'-carbonyldiimidazole.

The reaction between the activated derivative of the compound of formula (II) and the amine of formula (III) is typically conducted in an organic solvent. Suitable solvents include dimethylformamide and dichloromethane. The steps of activating the compound of formula (II) and treating the resulting activated derivative with the amine of formula (III) may take place without intermediate isolation of the activated derivative. In that case the process typically comprises combining the activating agent or coupling agent with the compound of formula (II) in an organic solvent and adding to the resulting reaction mixture the amine of formula (III).

A compound of formula (II) may be prepared by a process which comprises:
(a) treating a 2-halo-3-nitrobenzoic acid of formula (IV):

(IV)

wherein Hal is Cl, Br, I or F, with a heteroaromatic amine of formula (V):

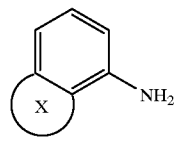

(V)

wherein X is as defined above for formula (I); and
(b) submitting the resulting compound of formula (VI):

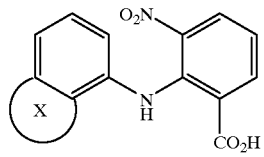

(VI)

wherein X is as defined above, to reductive cyclisation.

Step (a) is typically conducted in an organic solvent. Suitable examples include butane-2,3-diol, ethylene glycol and isopropanol. Step (b) is generally carried out by treatment of the compound of formula (V) with $NaBH_4$ in sodium methoxide, sodium ethoxide or aqueous NaOH. The process is described in J. Med. Chem. 1987, 30, 843–851.

Amines of formula (III) are known and commercially available compounds or may be produced from commercially available starting materials using conventional techniques, for instance as described in reference example 2 which follows.

A compound of formula (I) may be converted into another compound of formula (I) by conventional methods, for instance a compound containing a $C_1$–$C_6$ alkoxy group may be converted into a compound containing a hydroxy group, for instance by treatment with hydrobromic acid in glacial acetic acid or with boron tribromide in a halogenated hydrocarbon solvent, for instance dichloromethane, or with sodium thioethoxide in dimethyl formamide.

Heteroaromatic[a]phenazine carboxamide deriviatives may be converted into pharmaceutically acceptable salts, and salts may be converted into the free compound, by conventional methods. Pharmaceutically acceptable salts of the heteroaromatic[a]phenazine carboxamide derivatives of formula (I) include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid.

Multi-drug resistance (MDR) is a phenomenon whereby cells which are typically sensitive to chemotherapeutic agents develop resistance to those agents and to a wide range of unrelated drugs. MDR represents a major obstacle in the successful clinical therapy of cancer. Cancer cells which exhibit MDR can display a number of diverse cellular alterations including overexpression of P-glycoprotein (P-gp), overexpression of multidrug resistance associated protein (MRP), reduction in levels of topoisomerase II (termed atypical drug resistance) and qualitative changes in expression of topoisomerase I. MDR is a very important clinical problem with many tumors developing resistance to many chemotherapeutic agents including those that specifically target topoisomerase I and/or topoisomerase II.

By simultaneously inhibiting topoisomerase I and II, compounds such as DACA (Finlay et al, Eur. J. Cancer 32A, 708–714, 1996) have shown no loss of activity when resistance develops to camptothecin or amsacrine due to alteration of either topoisomerase I or II respectively. Qualititively different cell cycle events have been obtained with inhibitors of topoisomerase I or II. (Kaufman, Biochim. Biophys. Acta 1400, 195–212, 1998). Joint inhibitors of topoisomerase I and II appear to combine the properties of the individual specific inhibitors and act across the cell cycle (Haldane et al, Cancer Chemother. Pharmacol. 32: 463–470, 1993), resulting in a greater antitumour activity (Riou et al, Cancer Res. 53, 5987–5993, 1993).

MDR due to the overexpression of membrane transporters such as P-glycoprotein (Gottesman et al, Annu. Rev. Biochem. 62, 385–427, 1993) and MRP (Loe et al, Eur. J. Cancer 32A, 945–957, 1996) is known to reduce the clinical efficacy of chemotherapeutic agents such as paclitaxel, etoposide and doxorubicin. Agents that avoid such MDR mechanisms are predicted to show therapeutic benefit in the treatment of cancer.

Heteroaromatic[a]phenazine carboxamide derivatives of formula I and their pharmaceutically acceptable salts (hereinafter referred to as "the present compounds") have been found in biological tests to have activity as inhibitors of topoisomerase I and II. In one aspect of the invention the present compounds are joint inhibitors of topoisomerase I and topoisomerase II.

The present compounds may therefore be used as inhibitors of topoisomerase I. Alternatively the present compounds may be used as inhibitors of topoisomerase II. In a further embodiment they may be used as joint inhibitors of topoisomerase I and topoisomerase II. They have been shown to kill human tumour cells and avoid MDR mechanisms. They therefore have potential in the treatment of cancer. Examples of types of cancer that the present compounds can be used to treat include leukaemias, lymphomas, sarcomas, carcinomas and adenocarcinomas. Specific examples include breast, colon, brain, lung, ovary, pancreatic, stomach and skin cancer.

A human or animal patient harbouring a tumour may be treated by a method comprising the administration thereto of one of the present compounds. In particular, a method of treating human tumours, including those which express MDR, for instance the types of MDR referred to above, comprises administering a therapeutically effective amount of one of the present compounds to a patient harbouring a tumour. All types of tumour may thus be treated, both those which express MDR and those which do not. The present compound is administered in an amount effective to reduce or eliminate the tumour. In one aspect of the invention the present compound is administered orally. In another aspect the present compound is administered by a parenteral route, for instance intravenously.

Owing to their activity as inhibitors of topoisomerase I and topoisomerase II the present compounds may also be used as antiviral, antibacterial or antifungal agents.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 500 mg/kg, most commonly in the range of 0.01 to 100 mg/kg body weight. Such a dosage may be given, for example, from 1 to 5 times daily by bolus infusion, infusion over several hours and/or repeated administration.

A hetreoaromatic[a]phenazine carboxamide derivative of formula (I) or a pharmaceutically acceptable salt thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use in the treatment of tumours, including those which express MDR, comprising one of the present compounds is therefore provided.

The present compounds may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occuring phosphatides, for example soy bean lecithin, and esters or partial esters derived from fatty acids an hexitol anhydrides, for example sorbitan monooleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrastemally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic parentally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

Daily dosages can vary within wide limits and will be adjusted to the individual requirements in each particular case. In general, for administration to adults, an appropriate daily dosage is in the range of about 5 mg to about 500 mg, although he upper limit may be exceeded if expedient. The daily dosage can be administered as a single dosage or in divided dosages.

The invention will be further illustrated in the Examples which follow.

REFERENCE EXAMPLE 1
Preparation of Compounds of General Formula (II)

Reference Example 1A: Preparation of 4-Methoxypyrido-[2,3-α]phenazine-11-carboxylic Acid (II.1)

4-Methoxy-8-aminoquinoline (1.15 g, 6.6 mmol), 2-iodo-3-nitrobenzoic acid (3.87 g, 13.2 mmol) and a catalytic amount of Cu/CuI in N-ethylmorpholine (10 mL) and isopropanol (10 mL) was heated for 2 days at 70° C. The reaction mixture was boiled in aq $NH_3$ and charcoal/celite, filtered, and the filtrate acidified with conc. HCl. The resulting precipitate was collected and recrystallized from MeOH/$H_2O$ to give 2-(4-methoxy-8-quinolineamino)-3-nitrobenzoic acid (1.6 g, 74%): mp (MeOH/$H_2O$) 228–231 (dec) ° C. $^1$H NMR [$(CD_3)_2SO$] δ 4.21 (s, 3 H, $OCH_3$), 7.22 (d, J=7.9 Hz, 1 H, ArH), 7.23 (d, J=8.0 Hz, 1 H, ArH), 7.36 (br, 1 H, ArH), 7.48 (t, J=7.8 Hz, 1 H, ArH), 7.8 6 (d, J=7.9 Hz, 1 H, ArH), 8.17 (dd, J=8.2, 1.5 Hz, 1 H, H-4 or H-6), 8.25 (dd, J=7.7, 1.5 Hz, 1 H, H-4 or H-6), 8.95 (d, J=5.6 Hz, 1 H, ArH), 10.40 (br s, 1 H, NH), 13.5 (br, 1 H, $CO_2H$).

Reductive ring closure of 2-(4-methoxy-8-quinolineamino)-3-nitrobenzoic acid in 5 N NaOH/$NaBH_4$ gave 4-methoxy pyrido[2,3-α]phenazine-11-carboxylic acid (71%): mp (MeOH/$H_2O$) 281–285° C. $^1$H NMR ($CF_3CO_2D$) δ 4.62 (s, 3 H, $OCH_3$), 7.95 (d, J=7.7 Hz, 1 H, H-3), 8.53 (dd, J=8.9, 7.3 Hz, 1 H, H-9), 8.76 (d, J=9.7 Hz, 1 H, H-5), 8.96 (dd, J=8.9, 1.2 Hz, 1 H, H-8), 8.98 (d, J=9.7 Hz, 1 H, H-6), 9.16 (dd, J=7.2, 1.1 Hz, 1 H, H-10), 9.37 (d, J=7.1 Hz, 1 H, H-2).

Reference Example 1B
Preparation of Pyrido[3,4-α]phenazine-11-carboxylic Acid (II.2)

Reaction of 8-aminoisoquinoline with 2-iodo-3-nitrobenzoic acid (prepared by the method of Denny et al. *J. Med. Chem.*, 1990, 33(2), 814–819.) gave 2-(8-isoquinolineamino)-3-nitrobenzoic acid (5% yield): $^1$H NMR [$(CD_3)_2SO$] δ 6.96 (d, J=7.3 Hz, 1 H, ArH), 7.21 (m, 1 H, ArH), 7.54–7.61 (m, 2 H, ArH), 7.92 (br, 1 H, ArH), 8.10 (d, J=8.0 Hz, 2 H, ArH), 8.34 (br, 1 H, ArH), 8.63 (br, 1 H, ArH), 9.56 (br, 1 H, NH), 10.66 (br, 1 H, $CO_2H$). This material was used crude in the next step below.

Reductive ring closure of 2-(8-isoquinolineamino)-3-nitrobenzoic acid with 8 N NaOH/$NaBH_4$ as above gave pyrido[3,4-α]phenazine-11-carboxylic acid (86%): ¹H NMR (CF₃CO₂D) δ 8.50 (dd, J=8.6, 7.5 Hz, 1 H, H-9), 8.66 (d, J=9.5 Hz, 1 H, H-5 or H-6), 8.81 (d, J=6.3 Hz, 1 H, H-3 or H-4), 9.00 (d, J=8.8 Hz, 1 H, H-8), 9.06 (d, J=9.4 Hz, 1 H, H-5 or H-6), 9.23 (d, J=6.3 Hz, 1 H, H-3 or H-4), 9.29 (d, J=7.2 Hz, 1 H, H-10), 10.80 (s, 1 H, H-1). This crude compound was used directly in the preparation of compound 2.

Reference Example 1C
Preparation of Pyrido[4,3-α]phenazine-11-carboxylic Acid (II.3)

5-Aminoisoquinoline (1.42 g, 9.85 mmol), 2-bromo-3-nitrobenzoic acid (prepared by the method of Culhane. *Organic Syntheses*, 125–126) (2.0 g, 8.13 mmol), copper (I) iodide (0.1 g), copper powder (1.5 g) in N-ethylmorpholine (5 mL) and isopropanol (5 mL) was heated to 90° C. and stirred overnight at this temperature. The reaction mixture was then diluted with aqueous NaOH (7%), and insoluble copper salts were removed by filtration. The filtrate was washed with CH₂Cl₂ to remove any unreacted amine, and the aqueous layer was exactly neutralized with conc HCl. The resulting precipitate was filtered, washed with water, extracted into aqueous methanesulfonic acid, and filtered to remove any insoluble material. The filtrate was exactly neutralized with aqueous NaOH to give 2-(5-isoquinolineamino)-3-nitrobenzoic acid (0.22 g, 7%): mp (MeOH/H₂O) 264–268° C.; ¹H NMR [(CD₃)₂SO] δ □7.14 (d, J=7.5 Hz, 1 H, ArH), 7.20 (t, J=8.0 Hz, 1 H, ArH), 7.50 (t, J=7.9 Hz, 1 H, ArH), 7.82 (d, J=8.2 Hz, 1 H, ArH), 8.05 (br, 1 H, ArH), 8.12 (d, J=8.1 Hz, 1 H, ArH), 8.28 (dd, J=7.5, 1.2 Hz, 1 H, ArH), 8.63 (br, 1 H, ArH), 9.36 (br, 1 H, ArH), 10.26 (br s, 1 H, CO₂H).

The 2-(5-isoquinolineamino)-3-nitrobenzoic acid (0.22 g, 0.64 mmol) was dissolved in a solution of 2 M NaOEt in EtOH (10 mL), and NaBH₄ (0.12 g, 3.2 mmol) was then added. The mixture was heated under reflux for 4 h, then EtOH was removed by evaporation. The resulting residue was dissolved in water (20 mL) and neutralized with AcOH, and the crude product was choromatographed on silica gel, eluting with CH₂Cl₂/MeOH (50:1) to give pyrido[4,3-α]phenazine-11-carboxylic acid (0.12 g, 60%): mp (MeOH/H₂O) 294–298° C.; ¹H NMR [(CD₃)₂SO] δ 8.13–8.19 (m, 2 H, 2xArH), 8.42–8.44 (m, 2 H, 2xArH), 8.52 (dd, J=8.7, 1.0 Hz, 1 H, H-10), 8.91 (d, J=5.5 Hz, 1 H, H-1 or H-2), 9.05 (d, J=5.3 Hz, 1 H, H-1 or H-2), 9.51 (s, 1 H, H-4), 14.00 (br, 1 H, CO₂H).

Reference Example 1D
Preparation of 4-Methoxypyrido[4,3-a]phenazine-11-carboxylic Acid (II.4)

Reaction of 5-amino-1-methoxyisoquinoline with 2-bromo-3-nitrobenzoic acid at 65–70° C. gave 2-(1-methoxy-5-isoquinolineamino)-3-nitrobenzoic acid (quantitative yield): mp (MeOH/H₂O) 208–211° C.; ¹H NMR [(CD₃)₂SO] δ 4.08 (s, 3 H, OCH₃), 7.12 (d, J=7.5 Hz, 1 H, ArH), 7.17 (t, J=7.7 Hz, 1 H, H-7'), 7.41 (t, J=8.0 Hz, 1 H, H-3), 7.57 (d, J=6.0 Hz, 1 H, H-3' or H-4'), 7.87 (d, J=8.2 Hz, 1 H, ArH), 8.09 (d, J=8.0 Hz, 1 H, ArH), 8.10 (d, J=5.6 Hz, 1 H, H-3' or H-4'), 8.27 (d, J=7.1 Hz, 1 H, ArH), 10.32 (br, 1 H, CO₂H).

Reductive ring closure of 2-(1-methoxy-5-isoquinolineamino)-3-nitrobenzoic acid with 8N NaOH/NaBH₄ as above gave 4-methoxy-pyrido[4,3-α]phenazine-11-carboxylic acid (39%): mp (MeOH) 296–299° C.; ¹H NMR [CDCl₃] δ 4.25 (s, 3 H, OCH₃), 8.10–8.16 (m, 2 H, H-9 & H-5 or H-6), 8.39 (d, J=5.7 Hz, 1 H, H-1 or H-2), 8.57 (d, J=5.4 Hz, 1 H, H-1 or H-2), 8.58 (d, J=10.3 Hz, 1 H, H-5 or H-6), 8.61 (dd, J=8.7, 1.4 Hz, 1 H, H-8), 9.04 (dd, J=7.4 Hz, 1.4 Hz, 1 H, H-10), 15.49 (br, 1 H, CO₂H).

Reference Example 1E
Preparation of Pyrido[3,2-α]phenazine-11-carboxylic Acid (II.5)

Reaction of 5-aminoquinoline with 2-bromo-3-nitrobenzoic acid gave 2-(5-quinolineamino)-3-nitrobenzoic acid (13%): mp (MeOH/H₂O) 180–184° C.; ¹H NMR [(CD₃)₂SO] δ 6.98 (d, J=7.6 Hz, 1 H, ArH), 7.17 (t, J=7.9 Hz, 1 H, ArH), 7.55 (t, J=8.0 Hz, 1 H, ArH), 7.63 (dd, J=8.5, 4.2 Hz, 1 H, ArH), 7.72 (d, J=8.4 Hz, 1 H, ArH), 8.09 (dd, J=8.1, 1.2 Hz, 1 H, ArH), 8.27 (d, J=7.7 Hz, 1 H, ArH), 8.63, (brd, J=8.4 Hz, 1 H, ArH), 8.96 (br, 1 H, ArH), 10.31 (brs, 1 H, NH), 13.6 (br s, 1 H, CO₂H).

Reductive ring closure of 2-(5-quinolineamino)-3-nitrobenzoic acid with NaOEt/NaBH₄ as above gave pyrido[3,2-α]phenazine-11-carboxylic acid (42%): mp (MeOH/H₂O) 280–282° C.; ¹H NMR [(CD₃)₂SO] δ 7.97 (dd, J=8.2, 4.4 Hz, 1 H, ArH), 8.12 (dd, J=8.4, 7.1 Hz, 1 H, ArH), 8.30–8.36 (m, 2 H, 2xArH), 8.44 (d, J=6.6 Hz, 1 H, ArH), 8.53 (d, J=8.7 Hz, 1 H, ArH), 9.19 (dd, J=4.4, 1.7 Hz, 1 H, ArH), 9.43 (dd, J=8.2, 1.4 Hz, 1 H, ArH), 13.90 (br, 1 H, CO₂H).

Reference Example 1F
Preparation of Pyrazino [2,3-α]phenazine-11-carboxylic Acid (II.6)

A mixture of 5-aminoquinoxaline (1.0 g, 6.89 mmol), 2-bromo-3-nitrobenzoic acid (4.0 g, 13.78 mmol), Cu/CuI (catalytic) and N-ethylmorpholine (5 mL) in isopropanol (5 mL) was heated at 65–70° C. overnight. The mixture was then dissolved in aqueous ammonia, treated with charcoal/Celite, and filtered. The filtrate was acidified with conc. HCl, and the resulting precipitate was collected while the mixture was still warm and washed with water (to remove unreacted 2-bromo-3-nitrobenzoic acid). It was then dried and chromatographed on silica gel, eluting with CH₂Cl₂/MeOH (19:1), to give 3-nitro-(quinoxalinylamino)benzoic acid (0.9 g, 42%): mp (MeOH) 232–237° C.; ¹H NMR [(CD₃)₂SO] δ 6.92–6.97 (m, 1 H, ArH), 7.30 (t, J=8.0 Hz, 1 H, ArH), 7.62–7.66 (m, 2 H, 2xArH), 8.23 (dd, J=8.2, 1.6 Hz, 1 H, ArH), 8.29 (dd, J=7.8, 1.6 Hz, 1 H, ArH), 8.97 (d, J=1.7 Hz, 1 H, H-2' or H-3'), 9.03 (d, J=1.9 Hz, 1 H, H-2' or H-3'), 10.73 (br s, 1 H, NH), 13.8 (br s, 1 H, CO₂H).

A solution of 3-nitro-(quinoxalinylamino)benzoic acid (0.8 g, 2.58 mmol) in 5M NaOH (40 mL) was treated with NaBH₄ (0.9 g, 12.9 mmol), and the mixture was heated under reflux for 2 h. The cooled mixture was diluted with water (40 mL), then neutralized with glacial AcOH to give pyrazino[2,3-α]phenazine-11-carboxylic acid (0.52 g, 73%): mp (MeOH/Et₃N/AcOH)>350° C. ¹H NMR [CF₃CO₂D] δ 8.62 (dd, J=8.8, 7.3 Hz, 1 H, H-9), 8.91 (d, J=9.8 Hz, 1 H, H-5 or H-6), 8.97 (d, J=9.8 Hz, H-5 or H-6), 9.18 (dd, J=8.8, 1.0 Hz, 1 H, H-8), 9.47 (dd, J=7.3, 1.0 Hz, 1 H, H-10), 9.57 (d, J=2.2 Hz, 1 H, H-2 or H-3), 9.65 (d, J=2.2 Hz, 1 H, H-2 or H-3),

Reference Example 1G
Preparation of 1H-pyrazolo[3,4-α]phenazine-10-carboxylic Acid (II.7)

Hydrogenation of 7-nitroindazole (prepared from 2-methyl-6-nitroaniline according to the literature procedures. Davies, R. R. *J.C.S.*, 1955, 2412–2423; Porter, H. D *Org. Synth. Collect.* Vol I, 20, 73–74.) gave 7-aminoindazole. This was reacted as above with 2-iodo-3-nitrobenzoic acid to give 2-(1H-indazol-7-ylamino)-3-nitrobenzoic acid (19%, crude). This was purified by treating with an ethereal solution of CH₂N₂ followed by chromatography on silica gel to give methyl 2-(1H-indazol-7-ylamino)-3-nitrobenzoate (72%); mp (EtOAc/n-hexane) 137–138° C.; ¹H NMR [(CD₃)₂SO] δ 3.49 (s, 3 H, OCH₃), 6.72 (br d, J=7.2 Hz, 1 H, ArH), 6.91 (t, J=7.7 Hz, 1 H, ArH), 7.17 (t, J=8.0 Hz, 1 H, ArH), 7.45 (d, J=8.0 Hz, 1 H, ArH), 8.07–8.12 (m, 2 H, 2xArH), 8.18 (dd, J=8.2, 1.5 Hz, 1 H, ArH), 9.45 (br s, 1 H, diphenylamine NH), 13.36 (br s, 1 H, indazole NH). Also isolated was methyl 2–8 (1-methyl-1H-indazol-7-yl)amino]-3-nitrobenzoate (3%); mp (EtOAc/n-hexane) 137–138° C.; $^1$H NMR [(CD$_3$)$_2$SO] δ 3.72 (s, 3 H, OCH$_3$), 4.19 (s, 3 H, NCH$_3$), 6.46 (d, J=7.2 Hz, 1 H, ArH), 6.83 (dd, J=8.2, 7.4 Hz, 1 H, ArH), 7.18 (t, J=8.0 Hz, 1 H, ArH), 7.30 (d, J=8.3 Hz, 1 H, ArH), 8.18–8.22 (m, 2 H, 2xArH), 8.34 (s, 1 H, ArH), 9.97 (s, 1 H, NH).

Reductive cyclisation of methyl 2-(-1H-indazol-7-ylamino)-3-nitrobenzoate with NaBH$_4$ in 2 M NaOH as above gave 1H-pyrazolo[3,4-α]phenazine-10-carboxylic acid yellow solid (65%) $^1$H NMR [(CD$_3$)$_2$SO] δ 7.72 (br d, J=9.1 Hz, 1 H, H-4), 8.12 (dd, J=8.6, 7.2 Hz, 1 H, H-8), 8.24 (br d, J=9.2 Hz, 1 H, H-5), 8.51 (br s, 1 H, H-3), 8.55 (dd, J=8.6, 1.4 Hz, 1 H, H-7 or H-9), 8.62 (dd, J=7.2, 1.2 Hz, 1 H, H-9 or H-7), 14.71 (v br s, 2 H, NH and CO$_2$H).

Reference Example 1H
Preparation of 1-Methyl-1H-pyrazolo [3,4-α]phenazine-10-carboxylic Acid (II.8)

Reaction of 7-amino-1-methylindazole and 2-iodo-3-nitrobenzoic acid as above gave 2–8 (1-methyl-1H-indazol-7-yl)amino]-3-nitrobenzoic acid (33% yield); mp (EtOAc/n-hexane) 240–244° C.; $^1$H NMR [(CD$_3$)$_2$SO] δ 4.33 (s, 3 H, NCH$_3$), 6.55 (d, J=7.5 Hz, 1 H, ArH), 6.84 (t, J=7.7 Hz, 1 H, ArH), 6.90 (t, J=7.7 Hz, 1 H, ArH), 7.36 (d, J=7.9 Hz, 1 H, ArH), 7.80 (dd, J=8.1, 1.7 Hz, 1 H, ArH), 8.00 (s, 1 H, ArH), 8.31 (dd, J=7.5, 1.7 Hz, 1 H, ArH), 13.47 (br s, 1 H, COOH).

Reductive cyclisation of 2–8 (1-methyl-1H-indazol-7-yl)amino]-3-nitrobenzoic acid with NaBH$_4$ in 2 M NaOH was carried out as above gave 1-methyl-1H-pyrazolo[3,4-α]phenazine-10-carboxylic acid (34%); mp (acetone) 294–296° C.; $^1$H NMR [(CD$_3$)$_2$SO] δ 4.76 (s, 3 H, NCH$_3$), 7.75 (d, J=9.2 Hz, 1 H, H-4 or H-5), 8.06 (dd, J=8.6, 7.1 Hz, 1 H, H-8), 8.21 (d, J=9.2 Hz, 1 H, H-5 or H-4), 8.29 (s, 1 H, H-3), 8.36 (dd, J=7.0, 1.3 Hz, 1 H, H-7 or H-9), 8.45 (dd, J=8.7, 1.4 Hz, 1 H, H-7 or H-9), 13.60 (v br s, 1 H, COOH).

Reference Example 1I
Preparation of 3H-pyrazolo[4,3-a]phenazine-10-carboxylic Acid (II.9)

4-Nitroindazole (prepared according to the literature procedures. Davies, R. R. *J.C.S.*, 1955, 2412–2423; Porter, H. D. *Org. Synth. Collect. Vol I*, 20, 73–74.) (10.0 g, 61.4 mmol) was hydrogenated in absolute EtOH (400 mL) in the presence of Pd/C (2 g) to give crude 4-aminoindazole (8.06 g, 99%), which was used directly. A mixture of (7.0 g, 52.6 mmol), 2-bromo-3-nitrobenzoic acid-(12.9 g, 52.6 mmol), Cu powder (250 mg) and CuI (500 mg) were heated with stirring at 70° C. for 3 days in a mixture of isopropanol (25 mL) and N-ethylmorpholine (8 mL). The cooled mixture was neutralized with glacial AcOH, then diluted with water (100 mL) and filtered through Celite. The Celite pad was washed well with water (300 mL) and EtOAc (300 mL), and the the aqueous phase of the filtrate was further extracted with EtOAc (2×300 mL). The combined EtOAc fractions were dried (Na$_2$SO$_4$) and evaporated under reduced pressure. The residue was chromatographed on silica gel, eluting with CH$_2$Cl$_2$/MeOH (4:1), to give give impure 2-(1H-indazol-4-ylamino)-3-nitrobenzoic acid as an orange solid (2.82 g, 17%). Purification was by treatment with an ethereal solution of CH$_2$N$_2$ followed by chromatography on silica gel to give gave methyl 2-(1H-indazol-4-ylamino)-3-nitrobenzoate (1.15 g, 39% overall); mp (EtOAc/hexane) mp 152–153.5° C.; $^1$H NMR [(CD$_3$)$_2$SO] δ 3.59 (s, 3 H, OCH$_3$), 6.36–6.41 (m, 1 H, ArH), 7.10–7.15 (m, 2 H, 2xArH), 7.25 (t, J=8.0 Hz, 1 H, ArH), 8.00 (br s, 1 H, ArH), 8.10–8.19 (m, 2 H, 2xArH), 9.51 (br s, 1 H, diphenylamine NH), 13.09 (br s, 1 H, indazole NH). Also isolated was methyl 2-](1-methyl-1H-indazol-4-yl)amino]-3-nitrobenzoate (68 mg, 3%); mp (EtOAc/hexane) 165–167° C.; $^1$H NMR [(CD$_3$)$_2$SO] δ 3.62 (s, 3 H, OCH$_3$), 4.16 (s, 3 H, NCH$_3$), 6.30 (d, J=7.2 Hz, 1 H, ArH), 7.02 (dd, J=8.4, 7.4 Hz, 1 H, ArH), 7.19–7.34 (m, 2 H, 2xArH), 8.10–8.18 (m, 2 H, 2xArH), 8.37 (s, 1 H, ArH), 9.49 (s, 1 H, NH).

A solution of methyl 2-(1H-indazol-4-ylamino)-3-nitrobenzoate (254 mg, 0.85 mmol) in 2 M NaOH (20 mL) was stirred at room temperature for 1 h to complete hydrolysis to 2-(1H-indazol-4-ylamino)-3-nitrobenzoic acid then NaBH$_4$ (194 mg, 5.11 mmol) was added and the mixture heated under reflux for 30 min. The mixture was then acidified with conc. HCl, then glacial AcOH, until the pH reached 5. This aqueous solution was then extracted with EtOAc (3×50 mL), the extracts combined and dried (Na$_2$SO$_4$), and the solvent removed under reduced pressure. Crystallization from acetone gave 3H-pyrazolo[4,3-a]phenazine-10-carboxylic acid (97 mg, 43%); mp 305–310° C.; $^1$H NMR [(CD$_3$)$_2$SO] δ 7.98 (br s, 1 H, H-4), 8.07 (dd, J=8.6, 7.2 Hz, 1 H, H-8), 8.20 (d, J=9.2 Hz, 1 H, H-5), 8.53 (dd, J=8.5, 1.3 Hz, 1 H, H-7 or H-9), 8.60 (dd, J=7.1, 1.3 Hz, 1 H, H-9 or H-7), 8.90 (v br s, 1 H, H-1), 14.26 (v br s, 1 H, NH or COOH), 14.76 (v br s, 1 H, NH or COOH).

Reference Example 1J
Preparation of 3-Methyl-3H-pyrazolo[4,3-a]phenazine-10-carboxylic Acid (II.10)

A solution of 4-nitroindazole (prepared according to the literature procedures Davies, R. R. *J.C.S.*, 1955, 2412–2423; Porter, H. D. *Org. Synth. Collect. Vol I*, 20, 73–74.) (2.01 g, 12.3 mmol) was added slowly to a cold (ice/water), stirred suspension of NaH (440 mg, 18.4 mmol) in DMF (20 mL) under N$_2$. The mixture was stirred for 30 min, and a solution of MeI (1.91 g, 13.5 mmol) in DMF (10 mL) was then added. Workup gave 1-methyl-4-nitroindazole (1.79 g, 82%); mp (EtOAc/petroleum ether) 138–139° C. Hydrogenation of this (6.70 g, 37.9 mmol) in absolute EtOH (300 mL) in the presence of Pd/C (1.00 g) gave 4-amino-1-methylindazole (4.23 g, 76%). A mixture of 4-amino-1-methylindazole (4.10 g, 27.9 mmol) and 2-bromo-3-nitrobenzoic acid (6.86 g, 27.9 mmol) were then reacted in a mixture of isopropanol/N-methylmorpholine in the presence of copper powder and CuI as above, giving 2-[(1-methyl-1H-indazol-4-yl)amino]-3-nitrobenzoic acid (439 mg, 5 %); mp (EtOAc/n-hexane) 257–260° C.; Reductive cyclisation of 2-[(1-methyl-1H-indazol-4-yl)amino]-3-nitrobenzoic acid with NaBH$_4$ in 2 M NaOH as above gave 3-methyl-3H-pyrazolo[4,3-a]phenazine-10-carboxylic acid as a dark yellow solid (54%); mp (acetone) 320–323° C. [(CD$_3$)$_2$SO] δ 4.28 (s, 3 H, NCH$_3$), 8.07 (t, J=7.9 Hz, 1 H, H-8), 8.10 (d, J=9.6 Hz 1H, H-4 or H-5), 8.39 (d, J=9.6 Hz 1H, H-4 or H-5), 8.52–8.60 (m, 2H, H-7 and H-9), 8.76 (s, 1 H, H-2), 14.90 (br s, 1 H, COOH).

Reference Example 1K
Preparation of 3H-Imidazo[4,5-α]phenazine-10-carboxylic Acid (II.11)

Reaction of 4-aminobenzimidazole (prepared by literature methods Rabinowitz, J. L. *J. Am. Chem. Soc.*, 1951, 73, 3030–3037; van der Want, G. M. *Rec. Trav. Chim.*, 1948, 67, 45–51) and 2-iodo-3-nitrobenzoic acid as above gave 2-(3H-benzimidazol-4-ylamino)-3-nitrobenzoic acid (25%, crude). Purification was by treatment with ethereal CH$_2$N$_2$ followed by chromatograph gave methyl 2-(3H-benzimidazol-4-ylamino)-3-nitrobenzoate (18% yield); mp (EtOAc/Et$_2$O) 146–148° C.; $^1$H NMR [(CD$_3$)$_2$SO] δ 3.69 (s, 3 H, OCH$_3$), 6.54 (br s, 1 H, ArH), 7.00 (t, J=7.9 Hz, 1 H, ArH), 7.11–7.19 (m, 2 H, 2xArH), 8.12–8.20 (m, 3 H, 3xArH), 10.06 (br s, diphenylamine NH), 12.51 (br s, 1 H, imidazole NH). Also isolated was methyl 2-[(3-methyl-3H-imidazol-4-yl)amino]-3-nitrobenzoate (6%); mp (EtOAc) 219–221° C.; $^1$H NMR [(CD$_3$)$_2$SO] δ 3.40 (s, 3 H, OCH$_3$), 4.09 (s, 3 H, NCH$_3$), 6.71 (d, J=7.6 Hz, 1 H, ArH), 6.96–7.05 (m, 2 H, 2xArH), 7.43 (d, J=8.0 Hz, 1 H, ArH), 7.99 (dd, J=7.7, 1.6 Hz, 1 H, ArH), 8.11 (dd, J=8.3, 1.5 Hz, 1 H, ArH), 8.15 (s, 1 H, ArH), 9.70 (s, 1 H, NH).

Reductive cyclisation of 2-(3H-benzimidazol-4-ylamino)-3-nitrobenzoate with NaBH$_4$ in 2 M NaOH as above gave 3H-imidazo[4,5-a]phenazine-10-carboxylic acid yellow solid (54% yield), mp (EtOAc/Et$_2$O) 225–227° C.; $^1$H NMR [(CD$_3$)$_2$SO] δ 2.63 [s, 6 H, N(CH$_3$)$_2$], 2.91 [t, J=5.4 Hz, 2 H, CH$_2$N(CH$_3$)$_2$], 3.87 (q, J=5.1 Hz, 2 H, CONHCH$_2$), 7.98 (dd, J=8.6, 7.2 Hz, 1 H, H-3), 8.04 (d, J=9.3 Hz, 1 H, H-6 or H-7), 8.28 (s, 1 H, H-9), 8.30 (d, J=9.3 Hz, 1 H, H-7 or H-6), 8.45 (dd, J=8.6, 1.3 Hz, 1 H, H-2 or H-4), 8.98 (dd, J=7.2, 1.3 Hz, 1 H, H-4 or H-2), 12.16 (br s, 1 H, CONH), 13.25 (v brs, 1 H, NH).

REFERENCE EXAMPLE 2
Preparation of Compounds of General Formula (III)

Reference Example 2A
(R)-N$^1$,N$^1$-Dimethyl-propane-1,2-diamine. Hydrochloride Salt (III.1)

2-(R)-[N-(tert-Butoxycarbonyl)amino]propanal was prepared from D-alanine Me-ester hydrochloride according to the procedure described in the literature (Chakravarty et al, J. Med. Chem 1989, p1886). A mixture of the aldehyde (16.21 g), dimethylamine hydrochloride (15.28 g), sodium acetate( 1.53 g) and sodium cyanoborohydride (8.24 g) in methanol (250 mL) was stirred at room temperature for 18 hours maintaining pH at 6–7 with AcOH. The reaction mixture was dissolved in ethyl acetate, washed with water, dried (MgSO$_4$), and the solvent removed in vacuo to yield a viscous oil which was purified using flash chromatography to yield the dimethylamino derivative as a white solid (10.81 g).

To this compound (3.17 g) was added a 4.0 M solution of hydrochloric acid in dioxane (20 mL) at room temperature. After stirring for 1 hour the volatiles were removed in vacuo to yield the desired title compound as a viscous oil (2.79 g).

Reference Example 2B
(S)-2-Amino-3-dimethylamino-propan-1-ol. Hydrochloride salt (III.2)

N-[(tert-Butoxy)carbonyl]-O-(tert-butyldimethylsilyl)-R-serine methyl ester was prepared according to the literature (H. W. Scheeren et al, J. Org. Chem. 1990, p3998) from D-serine methyl ester hydrochloride. Treatment of this compound with diisobutyl aluminium hydride in toluene at −70° C. for 2 hours yielded the corresponding aldehyde (H. W. Scheeren et al, J. Org. Chem. 1990, p3998). A mixture of the crude aldehyde (4.43 g), dimethylamine hydrochloride (2.26 g), sodium cyanoborohydride (1.31 g) and sodium acetate (1.83 g) was stirred in methanol (55 mL) for 24 hours at room temperature. Aqueous work-up yielded the dimethylamine derivative. This was dissolved in dioxane and to this was added a 4.0 M solution of hydrochloric acid in dioxane and the mixture stirred for 20 minutes. Concentration of the mixture in vacuo yielded the crude desired title compound as a white solid.

EXAMPLE 1

Preparation of Compounds of General Formula (I)

Example 1A

Pyrido[4,3-α]phenazine-11-carboxylic Acid (2-dimethylamino-ethyl)-amide

A mixture of pyrido[4,3-α]phenazine-11-carboxylic acid (II.3) (0.11 g, 0.38 mmol) and CDI (0.12 g, 0.76 mmol) in DMF (5 mL) was heated and stirred at 50–60° C. for 2 h. N,N-Dimethylethylenediamine (0.5 mL, excess) was then added, and the mixture was stirred at room temperature for 2 h. The DMF was removed under reduced pressure, and the residue was diluted with water. The resulting precipitate was collected and crystallized from CH$_2$Cl$_2$/hexane to give pyrido[4,3-α]phenazine-11-carboxylic acid (2-dimethylamino-ethyl)-amide (0.11 g, 84%): mp 213–215° C.; $^1$H NMR [CDCl$_3$] δ 2.48 [s, 6 H, N(CH$_3$)$_2$], 2.75 [t, J=5.7 Hz, 2 H, CH$_2$N(CH$_3$)$_2$], 3.89 (q, J=5.5 Hz, 2 H, CH$_2$NH), 8.03–8.14 (m, 3 H, 3xArH), 8.42 (dd, J=8.4, 1.5 Hz, 1 H, ArH), 9.00 (d, J=5.5 Hz, 1 H, H-1 or H-2), 9.07 (dd, J=7.2, 1.5 Hz, 1 H, H-10), 9.34 (s, 1 H, H-4), 9.36 (d, J=5.5 Hz, 1 H, H-1 or H-2), 10.66 (br, 1 H, CONH).

The following compounds of formula (I) were prepared in an analogous manner using the appropriate starting acid of formula (II) and amine of formula (III). The compounds were purified either by crystallization or using flash chromatography on either silica or alumina using organic solvents as eluents (such as 5% methanol in dichloromethane).

Pyrido[2,3-α]phenazine-11-carboxylic acid (2-dimethylamino-ethyl)-amide was prepared from pyrido [2,3-α]phenazine-11-carboxylic acid (II.1) and N,N-dimethylethylenediamine Pyrido[3,2-α]phenazine-11-carboxylic acid (2-dimethylamino-ethyl)-amide was prepared from pyrido [3,2-α]phenazine-11-carboxylic acid (II.5) and N,N-dimethylethylenediamine Pyrido [3,4-α]phenazine-11-carboxylic acid (2-dimethylamino-ethyl)-amide was prepared from pyrido [3,4-α]phenazine-11-carboxylic acid (II.2) and N,N-dimethylethylenediamine Pyrazino[2,3-α]phenazine-11-carboxylic acid (2-dimethylamino-ethyl)-amide was prepared from pyrazino [3,2-α]phenazine-11-carboxylic acid (II.6) and N,N-dimethylethylenediamine 4-Methoxypyrido [4,3-α]phenazine-11-carboxylic acid (2-dimethylamino-ethyl)-amide was prepared from 4-methoxypyrido[4,3-α]phenazine-11-carboxylic acid (II.4) and N,N-dimethylethylenediamine 4-Methoxypyrido [2,3-α]phenazine-11-carboxylic acid (2-dimethylamino-ethyl)-amide was prepared from 4-Methoxypyrido[2,3-α]phenazine-11-carboxylic acid (II.1) and N,N-dimethylethylenediamine 3-Methyl-3H-Pyrazolo[4,3-α]phenazine-10-carboxylic acid (2-dimethylamino-ethyl)-amide was prepared from 3-methyl-3H-Pyrazolo[4,3-α]phenazine-10-carboxylic acid (II.10) and N,N-dimethylethylenediamine 1-Methyl-1H-pyrazolo[3,4-α]phenazine-10-carboxylic acid (2-dimethylamino-ethyl)-amide was prepared from 1-methyl-1H-pyrazolo[3,4-α]phenazine-10-carboxylic acid (II.8) and N,N-dimethylethylenediamine 1H-Pyrazolo[3,4-α]phenazine-10-carboxylic acid (2-dimethylamino-ethyl)-amide was prepared from 1H-pyrazolo[3,4-α]phenazine-10-carboxylic acid (II.7) and N,N-dimethylethylenediamine 3H-Pyrazolo[4,3-α]phenazine-10-carboxylic acid (2-dimethylamino-ethyl)-amide was prepared from 3H-pyrazolo[4,3-α]phenazine-10-carboxylic acid (II.9) and N,N-dimethylethylenediamine 1H-Imidazo[4,5-α]phenazine-10-carboxylic acid (2-dimethylamino-ethyl)-amide was prepared from 1H-imidazo[4,5-α]phenazine-10-carboxylic acid (II.11) and N,N-dimethylethytenediamine 3-Methyl-3H-pyrrolo[3,2-α]phenazine-10-carboxylic acid (2-dimethylamino-ethyl)-amide was prepared from 3-methyl-3H-pyrrolo[3,2-α]phenazine-10-carboxylic acid and N,N-dimethylethylenediamine 4-Methoxypyrido [4,3-α]phenazine-11-carboxylic acid (2-dimethylamino-1-(S)-hydroxymethyl-ethyl)-amide was prepared from 4-methoxypyrido[4,3-α]phenazine-11-carboxylic acid (II.4) and (S)-2-Amino-3-dimethylamino-propan-1-ol 4-Methoxypyrido[4,3-α]phenazine-11-carboxylic acid (2-dimethylamino-1(R)-methylethyl)-amide was prepared from 4-methoxypyrido[4,3-α]phenazine-11-carboxylic acid (II.4) and (R)-$N^1,N^1$-Dimethyl-propane-1,2-diamine

EXAMPLE 2

Interconversion of compounds of Formula (I)

Compounds of Formula (I) prepared as described in Example 1 were converted into other compounds of Formula (I) as described below.

Example 2i

4-Hydroxypyrido[4,3-α]phenazine-11-carboxylic Acid (2-dimethylaminoethyl)-amide

4-Methoxypyrido[4,3-α]phenazine-11-carboxylic acid (2-dimethylamino-ethyl)-amide (0.056 g, 0.16 mmol) was dissolved in glacial AcOH (5 mL) and hydrobromic acid (48/50% w w; (2 mL). The mixture was refluxed for 30 min, then cooled and neutralized with solid NaHCO$_3$. The product was extracted into CH$_2$Cl$_2$ (3×25 mL) dried (Na$_2$SO$_4$) and evaporated to give 4-hydroxypyrido[4,3-α]phenazine-11-carboxylic acid (2-dimethylamino-ethyl)-amide (0.018 g, 33%): mp (CH$_2$Cl$_2$/hexane) 268–270° C. $^1$H NMR (CDCl$_3$) δ 2.32 [s, 6 H, N(CH$_3$)$_2$], 2.61 [t, J=5.9 Hz, 2 H, CH$_2$N (CH$_3$)$_2$], 3.69 (q, J=5.7 Hz, 2 H, CH$_2$NH), 7.70 (d, J=7.1 Hz, 1 H, H-2), 7.99 (d, J=7.1 Hz, 1 H, H-1), 8.11 (d, J=9.2 Hz, 1 H, H-5),8.14 (dd, J=8.5, 7.2 Hz, 1 H, H-9), 8.46 (dd, J=8.6, 1.4 Hz, 1 H, H-8), 8.52 (d, J=9.2 Hz, 1 H, H-6), 9.98 (t, J=5.1 Hz, 1 H, CONH), 12.16 (br, 1 H, OH).

4-Hydroxypyrido [2,3-α]phenazine-11-carboxylic acid (2-dimethylamino-ethyl)-amide was prepared in an analogous manner from 4-methoxyoxypyrido[2,3-α]phenazine-11-carboxylic acid (2-dimethylamino-ethyl)-amide

EXAMPLE 3

Biological Testing of Compounds of Formula (I)

The cytotoxicity of compounds of formula (I) was measured using the H69 parental (H69/P) human small cell lung carcinoma cell line and the drug resistant human small cell lung carcinoma cell line H69/LX4 which overexpresses P-glycoprotein (Pgp). The cytotoxicity, as measured by the IC$_{50}$ (concentration required to give 50% cell kill) in the H69/LX4 cell line divided by the cytotoxicity in the H69/P cell line gives an indication of the degree to which a compound is affected by Pgp-dependent MDR and is termed the resistance factor (Rf) of the compound.

H69/P and H69/LX4 cells were pipetted into 96-well tissue culture plates and then allowed to incubate at 37° C. for 4 h. A range of concentrations from 0.01 nM to 5 μM of compounds of formula (I) or the standards TAS-103, Doxorubicin and Topotecan were then added. The plates were incubated for 5–6 days before adding AlamarBlue to each well and returning the plates to the incubator for 5–8 h to allow colour development. The cell numbers in the plates at the end of this period were directly proportional to the absorbance measured at a wavelength of 570 nm (reference wavelength 600 nm).

The compounds of formula (I) were active in the range 5 nM to 5 μM. Specific results for selected compounds are listed in table 1.

TABLE 1

| Compound | H69/P IC$_{50}$(nM) | H69/LX4 IC$_{50}$(nM) | Rf |
|---|---|---|---|
| TAS-103 | 21 | 22 | 1.1 |
| Doxorubicin | 27.3 | 3700 | 135 |
| Topotecan | 15.9 | 61.5 | 3.9 |
| 2 | 88 | 56 | 0.6 |
| 3 | 123 | 133 | 1.1 |
| 5 | 21 | 26 | 1.3 |
| 6 | 24 | 29 | 1.2 |
| 9 | 24 | 28 | 1.2 |
| 13 | 109 | 97 | 0.9 |

The cytotoxicity of the compounds described herein was also measured using the COR-L23 parental (COR-L23/P) human non-small cell lung carcinoma cell line and also the drug resistant human non-small cell lung carcinoma cell line COR-L23/R which overexpresses multidrug resistance associated protein (MRP). The cytotoxicity, as measured by the IC$_{50}$ (concentration required to give 50% cell kill) in the L23/R cell line divided by the cytotoxicity in the L23/P cell line gives an indication of the degree to which a compound may be affected by MRP-dependant MDR and is termed the resistance factor (Rf) of the compound.

L23/P and L23/R cells were pipetted into 96-well tissue culture plates and then allowed to incubate at 37° C. for 4 h. A range of concentrations from 0.01 nM to 5 μM of compounds of formula (I) or the standards TAS-103, Doxorubicin and Topotecan were then added. The plates were incubated for 5–6 days before proliferation was assessed using the sulphurhodamine B (SRB) assay as described by Skehan et al, J Natl Cancer Inst 1990, 82, pp1107–1112.

Compounds were active in the range 1 nM to 5 μM. Specific examples are listed in Table 2.

TABLE 2

| Compound | L23/P IC$_{50}$(nM) | L23/R IC$_{50}$(nM) | Rf |
|---|---|---|---|
| TAS-103 | 16.3 | 22 | 1.3 |
| Doxorubicin | 20.3 | 326.8 | 16.1 |
| Topotecan | 13.6 | 20.8 | 1.5 |
| 2 | 22 | 56 | 2.5 |
| 3 | 48 | 71 | 1.5 |
| 5 | 14 | 16 | 1.1 |
| 6 | 12 | 15 | 1.3 |
| 9 | 4 | 6 | 1.5 |

The cytotoxicity of the compounds described herein was also measured using the Jurkat human leukaemia cell line (JL$_C$) and also the amsacrine-resistant Jurkat human leukaemia cell line (JL$_A$) and the doxorubicin-resistant Jurkat human leukaemia cell line (JL$_D$). The cytotoxicity, as measured by the IC$_{50}$ (concentration required to give 50% cell kill) in the JL$_A$ or JL$_D$ cell line divided by the cytotoxicity in the JL$_C$ cell line gives an indication of the degree to which a compound may be affected by atypical drug resistance and is termed the resistance factor (Rf) of the compound. The method used has been described previously (Finlay et al, Eur J. Cancer 32A, 708–714, 1996). Compounds were active in the range 1 nM to 5 μM. Specific examples are listed in Table 3.

TABLE 3

| Compound | $JL_C$ $IC_{50}$(nM) | $JL_A$ $IC_{50}$(nM) | $Rf(JL_A/JL_C)$ | $JL_D$ $IC_{50}$(nM) | $Rf(JL_D/JL_C)$ |
|---|---|---|---|---|---|
| TAS-103 | 5.4 | 302 | 55.9 | 384 | 71.1 |
| Doxorubicin | 7.0 | 25.9 | 3.7 | 109 | 15.6 |
| 2 | 28 | 84 | 3 | 78 | 2.8 |
| 3 | 74 | 235 | 2.8 | 52 | 0.7 |
| 5 | 17 | 12 | 0.7 | 12 | 0.7 |
| 6 | 10 | 7 | 0.7 | 9 | 0.9 |
| 13 | 44 | 44 | 1 | 48 | 1.1 |

Compounds were also studied for their ability to stabilize cleavable complexes in the presence of either topoisomerase I or II essentially as described previously (Finlay et al, Eur. J. Cancer 32A, 708–714, 1996). Presence of cleavable complexes was indicated by an increase in the number and intensity of bands observed after electrophoresis and auto-radiography. The results are expressed as the effective concentration range where an increase in cleavable complexes was observed relative to controls in the absence of drug. A number of compounds described herein were tested using these protocols and compounds showed poisoning of topoisomerase I and II in the range 0.01–20 $\mu$M. Specific examples are listed in Table 4.

TABLE 4

| | Effective concentration range ($\mu$M) | |
|---|---|---|
| Compound | Topoisomerase I | Topoisomerase II |
| TAS-103 | 0.3–10.0 | 0.3–10.0 |
| 5 | 0.1–3.0 | 0.1–3.0 |
| 6 | 0.1–3.0 | 0.1–3.0 |

EXAMPLE 4

Pharmaceutical Composition

Tablets, each weighing 0.15 g and containing 25 mg of a compound of the invention can be manufactured as follows:

Composition for 10,000 tablets

Compound of the invention (250 g)

lactose (800 g)

corn starch (415 g)

talc powder (30 g)

magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 5

Characterisation of Compounds of Formula (I)

The compounds prepared were characterised by proton N.M.R. spectroscopy. All proton NMR were performed at 400 MHz. The results are set out in the following table, including the melting points.

| Compound Number | Melting point ° C. | $^1$H N.M.R. data |
|---|---|---|
| 1 | 273–275 (hydrochloride) | [hydrochloride in D2O] $\delta$ d 8.52 (br, 1 H), 8.13 (d, J = 6.8 Hz, 1 H), 7.88 (d, J = 7.8 Hz, 1 H), 7.60 (dd, J = 7.4, 8.1 Hz, 1H), 7.56–7.51 (m, 2 H), 7.41 (d, J = 9.2 Hz, 1 H), 7.02 (d, J = 9.1 Hz, 1H), 3.75 (t, J = 6.5 Hz, 2H), 3.43 (t, J = 6.5 Hz, 2 H, 3.08 (s, 6H). |
| 2 | 213–215 | [CDCl$_3$] $\delta$ 2.48 [s, 6 H, N(CH$_3$)$_2$], 2.75 [t, J = 5.7 Hz, 2 H, CH$_2$N(CH$_3$)$_2$], 3.89 (q, J = 5.5 Hz, 2 H, CH$_2$NH), 8.03–8.14 (m, 3 H, 3xArH), 8.42 (dd, J = 8.4, 1.5 Hz, 1H, ArH), 9.00 (d, J = 5.5 Hz, 1 H, H-1 or H-2), 9.07 (dd, J = 7.2, 1.5 Hz, 1 H, H-10), 9.34 (s, 1 H, H-4), 9.36 (d, J = 5.5 Hz, 1 H, H-1 or H-2), 10.66 (br, 1 H, CONH) |
| 3 | 280–282 | [CDCl$_3$] $\delta$ 2.48 [s, 6 H, N(CH$_3$)$_2$], 2.77 [t, J = 5.5 Hz, 2 H, CH$_2$N(CH$_3$)$_2$], 3.92 (q, J = 6.8 Hz, 2 H, CH$_2$NH), 7.77 (dd, J = 8.2, 4.5 Hz, 1 H, H-2), 8.04 (dd, J = 8.6, 7.3 Hz, 1 H, H-9), 8.27 (d, J = 9.6 Hz, 1 H, H-5 or H-6), 8.34 (d, J = 9.4 Hz, 1 H, H-5 or H-6), 8.47 (dd, J = 8.6, 1.5 Hz, 1 H, H-8), 9.08 (dd, J = 7.3, 1.5 Hz, 1 H, H-10), 9.15 (dd, J = 4.5, 1.6 Hz, 1 H, H-3), 9.92 (d, J = 7.2 Hz, 1 H, H-1), 10.78 (br, 1 H, CONH). |
| 4 | 149–150 | [CDCl$_3$] $\delta$ 2.41 [s, 6 H, N(CH$_3$)$_2$], 2.91 [t, J = 6.7 Hz, 2 H, CH$_2$N(CH$_3$)$_2$], 3.91 (q, J = 6.2 Hz, 2 H, CH$_2$NH), 8.10 (dd, J = 8.5, 7.3 Hz, 1 H, H-9), 8.33 (d, J = 9.7 Hz, 1 H, H-5 or H-6), 8.37 (d, J = 9.5 Hz, 1 H, H-5 or H-6), 8.48 (dd, J = 8.7, 1.5 Hz, 1 H, H-8), 9.09 (dd, J = 7.2, 1.5 Hz, 1 H, H-10), 9.11 (d, J = 2.2 Hz, 1 H, H-2 or H-3), 9.12 (d, J = 2.2 Hz, 1 H, H-2 or H-3), 11.62 (br, 1 H, CONH). |
| 5 | 172–174 | [CDCl$_3$]$\delta$ 2.45 [s, 6 H, N(CH$_3$)$_2$], 2.75 [t, J = 5.8 Hz, 2 H, CH$_2$(NCH$_3$)$_2$], 3.9 (q, J = 5.6 Hz, 2 H, CH$_2$NH), $\delta$ 4.23 (s, 3 H, OCH$_3$), 8.04 (dd, J = 8.6, 7.2 Hz, 1 H, H-9), 8.08 (d, J = 9.5 Hz, 1 H, H-5 or H-6), 8.45 (dd, J = 8.6, 1.8 Hz, 1 H, H-8), 8.49 (d, J = 9.5 Hz, H-5 or H-6), 8.51 (d, J = 5.6 Hz, 1 H, H-1 or H-2), 8.94 (d, J = 5.7 Hz, 1 H, H-1 or H-2), 9.07 (dd, J = 7.2, 1.5 Hz, 1 H, H-10), 10.72 (br 1 H, CONH). |

-continued

| Compound Number | Melting point ° C. | ¹H N.M.R. data |
|---|---|---|
| 6 | 123–124 | [CDCl₃] δ 1.52 (3H, d, J = 6.4 Hz); 2.38 (6 H, s); 2.50–2.58 (1 H, dd, J5.6, 6.8 Hz); 2.82–3.00 (1 H, m, J = 4.0, 8.4 Hz), 4.23 (3H, s); 4.52–4.62 (1 H, m); 8.05(1 H, dd, J = 0.94, 7.4 Hz); 8.09 (1 H, d, J = 2.4 Hz); 8.44 (1 H, d, J = 1.3 Hz); 8.48–8.52 (2 H, m); 8.60 (1 H, d, J = 5.0 Hz); 9.08 (1 H, dd, J = 1.3, 6.0 Hz); 10.72 (1 H, br). |
| 7 | 194–196 | [CDCl₃]δ 2.47 [s, 6 H, N(CH₃)₂], 2.75 [t, J = 5.7 Hz, 2 H, CH₂(NCH₃)₂], 3.90 (q, J = 5.5 Hz, 2 H, CH₂NH), 7.81 (d, J = 5.2 Hz, 1 H, H-3 or H-4), 8.02–8.06 (m, 2 H, H-9 & H-5 or H-6), 8.22 (d, J = 9.2 Hz, 1 H, H-5 or H-6), 8.45 (dd, J 32 8.6, 1.6 Hz, 1 H, H-8), 9.01 (d, J = 5.2 Hz, 1 H, H-3 or H-4), 9.10 (dd, J = 7.3, 1.6 Hz, 1 H, H-10), 10.76 (br, 1 H, CONH), 10.87 (s, 1 H, H-1). |
| 8 | 180–181 | [CDCl₃]δ 2.41 [s, 6 H, N(CH₃)₂], 2.96 [t, J = 6.9 Hz, 2 H, CH₂(NCH₃)₂], 3.91 (q, J = 6.3 Hz, 2 H, CH₂NH), 4.14 (s, 3 H, OCH₃); 7.12 (d, J = 5.4 Hz, 1 H, H-3), 8.03 (d, J = 9.5 Hz, 1 H, H-5), 8.05 (dd, J = 8.5, 7.2 Hz, 1 H, H-9), 8.39 (dd, J = 8.6, 1.4 Hz, 1 H, H-8), 8.45 (d, J = 9.6 Hz, 1 H, H-6), 8.97 (d, J = 5.4 Hz, 1 H, H-2), 9.02 (dd, J = 7.2, 1.4 Hz, 1 H, H-10), 11.88 (br, s, 1 H, CONH). |
| 9 | 158–159 | [CDCl₃] δ 2.40 (6 H, s); 2.84–3.02 (2 H, m); 4.06–4.13 (1 H, m); 4.14–4.20 (1 H, m); 4.22 (3 H, s); 4.57–4.65 (1 H, m); 7.98–8.18 (2 H, m); 8.40–8.52 (3 H, m); 8.72 (1 H, d); 9.02 (1 H, d, J = 6.9 Hz); 10.02 (1H, br). |
| 10 | 268–270 | [CDCl₃]δ 2.32 [s, 6 H, N(CH₃)₂], 2.61 [t, J = 5.9 Hz, 2 H, CH₂(NCH₃)₂], 3.69 (q, J = 5.7 Hz, 2 H, CH₂NH), 7.70 (d, J = 7.1 Hz, 1 H, H-2), 7.99 (d, J = 7.1 Hz, 1 H, H-1), 8.11 (d, J = 9.2 Hz, 1 H, H-5), 8.14 (dd, J = 8.5, 7.2 Hz, 1 H, H-9), 8.46 (dd, J = 8.6, 1.4 Hz, 1 H, H-8), 8.52 (d, J = 9.2 Hz, 1 H, H-6), 9.98 (t, J = 5.1 Hz, 1 H, CONH), 12.16 (br, 1 H, OH). |
| 11 | 223–228 (dec) | [CDCl₃]δ 2.56 [s, 6 H, N(CH₃)₂], 2.77 [t, J = 5.2 Hz, 2 H, CH₂(NCH₃)₂], 3.89 (q, J = 5.2 Hz, 2 H, CONHCH₂), 6.69 (d, J = 7.5 Hz, 1 H, H-2), 7.91 (d, J = 7.6 Hz, 1 H, H-3), 8.05 (d, J = 9.47 Hz, 1 H, H-5), 8.08 (dd., J = 8.2, 6.7 Hz, 1 H, H-9), 8.49 (dd, J = 8.4, 1.5 Hz, 1 H, H-8), 8.75 9d, J = 9.3 Hz, 1 H, H-6), 9.06 (dd, J = 7.2, 1.5 Hz, 1 H, H-10), 10.42 (br, 1 H, CONH), 11.19 (br, 1 H, OH). |
| 12 | 257–260 | [CDCl₃]δ 2.36 [s, 6 H, N(CH₃)₂], 2.65 [t, J = 5.8 Hz, 2 H, CH₂(NCH₃)₂], 3.71 (q, J = 5.5 Hz, 2 H, CONHCH₂), 8.01 (d, J = 9.5 Hz, 1 H, H-6 or H-7), 8.03 (dd, J = 8.6, 7.3 Hz, 1 H, H-3), 8.32 (d, J = 9.6 Hz, 1 H, H-7 or H-6), 8.44 (dd, J = 8.5, 1.5 Hz, 1 H, H-2 or H-4), 8.81 (dd, J = 7.2, 1.5 Hz, 1 H, H-4 or H-2), 8.97 (s, 1 H, H-10), 10.89 (br t, J = 4.7 Hz, 1 H, CONH). |
| 13 | 204–205 | [(CD₃)₂SO] δ 2.21 [s, 6 H, N(CH₃)₂], 3.27–3.30 [m, obscured by H₂O, CH₂N(CH₃)₂], 3.59 (q, J = 6.5 Hz, 2 H, CONHCH₂), 4.75 (s, 3 H, NCH₃), 7.77 (d, J = 9.2 Hz, 1 H, H-6 or H-7), 8.07 (dd, J = 8.3, 7.2 Hz,1 H, H-3), 8.21 (d, J = 9.2 Hz, H-7 or H-6), 8.30 (s, 1 H, H-8), 8.38–8.43 (m, 2 H, H-2 and H-4), 9.21 (br t, J = 5.8 Hz, 1 H, CONH). |
| 14 | 230–232 | [CDCl₃]δ 2.40 [s, 6 H, N(CH₃)₂], 2.71 [t, J = 6.2 Hz, 2 H, CH₂(NCH₃)₂], 3.73 (q, J = 5.9 Hz, 2 H, CONHCH₂), 7.74 (d, J = 9.2 Hz, 1 H, H-6 or H-7), 8.09 (dd, J = 8.3, 7.4 Hz, 1 H, H-3), 8.23 (d, J = 9.2 Hz, 1 H, H-7 or H-6), 8.42–8.47 (m, 2 H, H-8 and H-2 or H-4), 8.77 (dd, J = 7.3, 1.4 Hz, 1 H, H-4 or H-2), 11.00 (br t, J = 5.0 Hz, 1 H, CONH), 14.50 (v br s, 1 H, indazole NH). |
| 15 | 258–260 | [CDCl₃]δ 2.41 [s, 6 H, N(CH₃)₂], 2.65 [t, J = 5.8 Hz, 2 H, CH₂(NCH₃)₂], 3.71 (q, J = 5.5 Hz, 2 H, CONHCH₂), 7.92 (d, J = 9.3 Hz, 1 H, H-6 or H-7), 8.03 (dd, J = 8.3, 7.3 Hz, 1 H, H-3), 8.16 (d, J = 9.3 Hz, 1 H, H-7 or H-6), 8.43 (dd, J = 8.6, 1.5 Hz, 1 H, H-2 or H-4), 8.79 (dd, J = 7.2, 1.5 Hz, 1 H, H-4 or H-2), 9.08 (s, 1 H, H-10), 10.93 (br t, J = 4.7 Hz, 1 H, CONH), indazole NH too broad to observe. |
| 16 | 225–227 | [CDCl₃]δ 2.63 [s, 6 H, N(CH₃)₂], 2.91 [t, J = 5.4 Hz, 2 H, CH₂(NCH₃)₂], 3.87 (q, J = 5.1 Hz, 2 H, CONHCH₂), 7.98 (dd, J = 8.6, 7.2 Hz, 1 H, H-3), 8.04 (d, J = 9.3 Hz, 1 H, H-6 or H-7), 8.28 (s, 1 H, H-9), 8.30 (d, J = 9.3 Hz, 1 H, H-7 or H-6), 8.45 (dd, J = 8.6, 1.3 Hz, 1 H, H-2 or H-4), 8.98 (dd, J = 7.2, 1.3 Hz, 1 H, H-4 or H-2), 12.16 (br s, 1 H, CONH), 13.25 (v br s, 1 H, NH). |
| 17 | 143–144 | [CDCl₃]δ 2.43 [s, 6 H, N(CH₃)₂], 2.77 [t, J = 6.1 Hz, 2 H, CH₂(NCH₃)₂], 3.87 (q, J = 5.7 Hz, 2 H, CH₂NH), 4.03 (s, 3 H, NCH₃), 7.79 (d, J = 3.0 Hz, 1 H, H-4 or H-5), 7.87–7.94 (m, 4 H, H-4 or H-5, H-1, 2 & 8), 8.39 (dd, J = 8.4, 1.5 Hz, 1 H, H-7), 9.00 (dd, J = 7.3, 1.5 Hz, 1 H, H-9), 11.45 (br, 1 H, CONH). |

Note: 2,2,2-trifluoro-1-(9-anthryl)ethanol added to NMR samples of homochiral compounds in order to determine the optical purity.

What is claimed is:

1. A compound selected from the group consisting of a heteroaromatic[a]phenazine carboxamide derivative of formula (I)

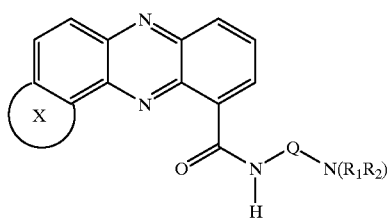

(I)

wherein X is a five- or six-membered heteroaromatic ring which contains one or two nitrogen atoms and which is unsubstituted or substituted by $C_1$–$C_6$ alkyl, hydroxyl or $C_1$–$C_6$ alkoxy;

Q is $C_1$–$C_6$ alkylene which is unsubstituted or substituted by $C_1$–$C_6$ alkyl which is unsubstituted or substituted by a hydroxy group; and $R_1$ and $R_2$ which are the same or different are each $C_1$–$C_6$ alkyl;

and the pharmaceutically acceptable salts thereof.

2. A compound according to claim 1 wherein the the heteroaromatic[a]phenazine carboxamide derivative is of formula (Ia)

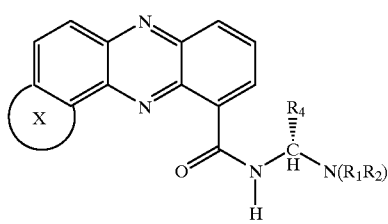

(Ia)

wherein $R_1$ and $R_2$ are as defined in claim 1 and $R_4$ is selected from the group consisting of (i) hydrogen, and (ii) $C_1$–$C_6$ alkyl which is unsubstituted or substituted by hydroxy.

3. A compound as defined in claim 1 which is selected from the group consisting of:

Pyrido[4,3-α]phenazine-11-carboxylic acid (2-dimethylamino-ethyl)-amide
Pyrido[2,3-α]phenazine-11-carboxylic acid (2-dimethylamino-ethyl)-amide
Pyrido[3,2-α]phenazine-11-carboxylic acid (2-dimethylamino-ethyl)-amide
Pyrido[3,4-α]phenazine-11-carboxylic acid (2-dimethylamino-ethyl)-amide
Pyrazino[2,3-α]phenazine-11-carboxylic acid (2-dimethylamino-ethyl)-amide
4-Methoxypyrido[4,3-α]phenazine-11-carboxylic acid (2-dimethylamino-ethyl)-amide
4-Methoxypyrido[2,3-α]phenazine-11-carboxylic acid (2-dimethylamino-ethyl)-amide
3-Methyl-3H-Pyrazolo[4,3-α]phenazine-10-carboxylic acid (2-dimethylamino-ethyl)-amide
1-Methyl-1H-pyrazolo[3,4-α]phenazine-10-carboxylic acid (2-dimethylamino-ethyl)-amide
1H-Pyrazolo[3,4-α]phenazine-10-carboxylic acid (2-dimethylamino-ethyl)-amide
3H-Pyrazolo[4,3-α]phenazine-10-carboxylic acid (2-dimethylamino-ethyl)-amide
1H-Imidazo[4,5-α]phenazine-10-carboxylic acid (2-dimethylamino-ethyl)-amide
3-Methyl-3H-indolo[2,3-α]phenazine-11-carboxylic acid (2-dimethylamino-ethyl)-amide
4-Methoxypyrido[4,3-α]phenazine-11-carboxylic acid (2-dimethylamino-1-(S)-hydroxymethyl-ethyl)-amide
4-Methoxypyrido [4,3-α]phenazine-11-carboxylic acid (2-dimethylamino-1(R) -methyl-ethyl)-amide
4-Hydroxypyrido[4,3-α]phenazine-11-carboxylic acid (2-dimethylamino-ethyl)-amide
4-Hydroxypyrido[2,3-α]phenazine-11-carboxylic acid (2-dimethylamino-ethyl)-amide and the pharmaceutically acceptable salts thereof.

4. A compound of formula (II):

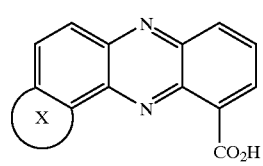

(II)

wherein X is as defined in claim 1, or a salt or ester thereof.

5. A pharmaceutical composition which comprises a pharmaceutically acceptable carrier or diluent and, as an active ingredient, a compound as defined in claim 1.

6. A method of treating a patient harboring a cancer selected from the group consisting of leukemias, lymphomas, sarcomas, carcinomas and adenocarinomas, which method comprises administering thereto an effective amount of a compound as claimed in claim 1.

7. A method according to claim 6 wherein the cancer expresses MDR.

8. A method according to claim 7 wherein the MDR is P-glycoprotein mediated MDR.

9. A method according to claim 7 wherein the MDR is MRP mediated MDR.

10. A method according to claim 7 wherein the MDR is atypical MDR.

11. A method of treating a patient suffering from a bacterial of fungal disease which method comprises administering thereto an effective amount of a compound as claimed in claim 1.

12. A method according to claim 6 wherein the cancer is selected from the group consisting of breast cancer, colon cancer, brain cancer, lung cancer, ovarian cancer, pancreatic cancer, stomach cancer and skin cancer.

13. A process for producing a compound as defined in claim 1, which process comprises:

(a) activating the carboxylic grouping of a compound of formula (II)

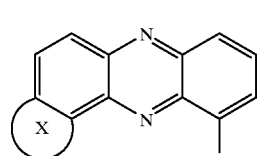

(II)

wherein X is as defined above;

(b) treating the compound resulting from step (a) with a compound of formula (III)

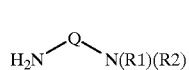
(III)

wherein Q, $R_1$ and $R_2$ are as defined above; and (c) if desired, converting one resulting heteroaromatic (a)phenazine carboxamide derivative into another such derivative, and/or converting a heteroaromatic[a]phenazine carboxamide derivative of formula (I) into a pharmaceutically acceptable salt thereof.

14. A process for producing a compound of formula (II) as defined in claim 4, which process comprises (a) treating a 2-halo-3-nitrobenzoic acid of formula (IV):

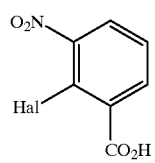
(IV)

wherein Hal is Cl, Br, I or F, with a heterocyclic amine of formula (V):

(V)

wherein X is as defined above for formula (I); and (b) treating the resulting compound of formula (VI):

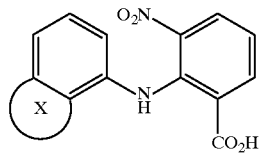
(VI)

wherein X is as defined above, with $NaBH_4$ in sodium methoxide, sodium ethoxide or aqueous NaOH.

* * * * *